US006434239B1

(12) United States Patent
DeLuca

(10) Patent No.: US 6,434,239 B1
(45) Date of Patent: Aug. 13, 2002

(54) ANTI-SOUND BEAM METHOD AND APPARATUS

(76) Inventor: Michael Joseph DeLuca, 1104 Claire Ave., Austin, TX (US) 78703

( * ) Notice: Subject to any disclaimer, the term of this patent is extended or adjusted under 35 U.S.C. 154(b) by 0 days.

(21) Appl. No.: 08/943,899

(22) Filed: Oct. 3, 1997

(51) Int. Cl.[7] .......................... A61F 11/06; G10K 11/16; H03B 29/00

(52) U.S. Cl. ......................... 381/71.2; 381/71.1; 381/77; 381/71.8

(58) Field of Search ............................... 381/71.1, 71.9, 381/71.3, 71.14, 77, 72, 94.1, 94.9

(56) References Cited

U.S. PATENT DOCUMENTS

| | | | | | |
|---|---|---|---|---|---|
| 4,654,871 | A | * | 3/1987 | Chaplin et al. | 381/72 |
| 4,823,908 | A | * | 4/1989 | Tanaka et al. | 181/175 |
| 4,829,590 | A | * | 5/1989 | Ghose | 455/63 |
| 4,982,434 | A | * | 1/1991 | Lenhardt et al. | 381/326 |
| 4,985,925 | A | * | 1/1991 | Langberg et al. | 381/71.6 |
| 5,663,727 | A | * | 9/1997 | Vokac | 341/132 |
| 5,727,071 | A | * | 3/1998 | Suzuki | 381/71.8 |
| 5,859,915 | A | * | 1/1999 | Norris | 381/77 |
| 5,889,870 | A | * | 3/1999 | Norris | 381/77 |

* cited by examiner

*Primary Examiner*—Xu Mei
(74) *Attorney, Agent, or Firm*—IdeoCo.com

(57) ABSTRACT

A device generates a directional anti-sound beam by modulating an ultrasonic carrier with a sound canceling signal and exciting an ultrasonic transducer with the modulated signal. When the anti-sound beam is directed at a sound source, the level of sound from the sound source is reduced. A microphone monitors the resultant sound for adjusting the sound canceling signal. An alternate signal may be further modulated upon the anti-sound beam to provide a substitute sound at the sound source.

20 Claims, 3 Drawing Sheets

ANTI-SOUND BEAM METHOD AND APPARATUS

FIELD OF THE INVENTION

This invention relates generally to the audio field and more specifically to transmission of sound canceling audio with a sound beam.

BACKGROUND OF THE INVENTION

Sound canceling techniques have become a growing application field with many systems designed to reduce sound in compartments such as automobile or aircraft cabins. However, such systems are designed to reduce the level of undesirable within a certain predetermined space by generating a sound canceling signal within the space. These methods do not attempt to cancel the sound generated at the sound source. Still another system has been designed to reduce sound generated by the sound source by actively quieting the sound source. See "Active control of Sound radiation from a simply supported beam: Influence of bending near field waves": C. Guirou, The Journal of the Acoustical Society of America, May 1993. What is needed is a method and apparatus capable of reducing sound at the source of the sound from a remote sound canceling source.

Furthermore, within an automobile compartment for example, sound canceling systems are designed to reduce the level of undesirable sound at a predetermined space, substantially around the occupant's ears. However outside the space, the undesirable sound and the sound canceling signal may become additive, thereby increasing the total level of undesirable sound beyond the predetermined space. Thus, what is needed is a method and apparatus capable of directing sound canceling signal into the predetermined space while limiting the additive affect of the sound canceling signal with the undesirable sound signal beyond the predetermined space.

DESCRIPTION OF A PREFERRED EMBODIMENT

The directionality of sound increases as the frequency of the sound increases. Thus, low frequency bass sounds are substantially omnidirectional while higher frequency treble sounds are more directional. Even more directional are ultrasonic signals which have been typically used in television remote control and other remote control applications. By modulating ultrasonic signals with audio signals, audio signals may be produced with the improved directionality of ultrasonic signals.

Such "sound beams" or "parametric arrays" are known in the art and have been demonstrated to produce highly directional audio sound by combining audio and ultrasonic signals. The sound beams can produce an audio signal that is highly directional as a result of an ultrasonic carrier signal, which is itself highly directional. See 1997 Discovery Magazine Technology Awards Expo at Epcot. Furthermore similar systems using the parametric arrays in air have been described. See "Parametric array in air", Bennett, Mary Beth, The Journal of the Acoustical Society of America, March, 1975, and U.S. Pat. No. 4,823,908 "Directional Loudspeaker System" to Takana et al., Apr. 25, 1989. Said references are hereby incorporated by reference.

Noise canceling devices are known in the art and have been developed for numerous applications, and often include a microphone to monitor sound within a particular region and generate a noise canceling signal in response thereto. Yet other variations include monitoring a characteristic of the noise generator in order to predict the type of noise to be canceled. For example the RPM (rotations per minute) of an engine of an automobile may be monitored in order to predict the noise inside of cabin of an automobile in order to generate a noise canceling signal.

By combining noise canceling sound with an ultrasonic carrier, the noise canceling signal may take on the directionality of the ultrasonic carrier, thus forming an "anti-sound beam". The anti-sound beam, when directed at a sound source reduces the sound generated by object, thus canceling the sound at the source, rather than in a predetermined space. Thus, other desirable sounds from other sound sources may be heard while undesirable sounds reduced.

Figure 1:
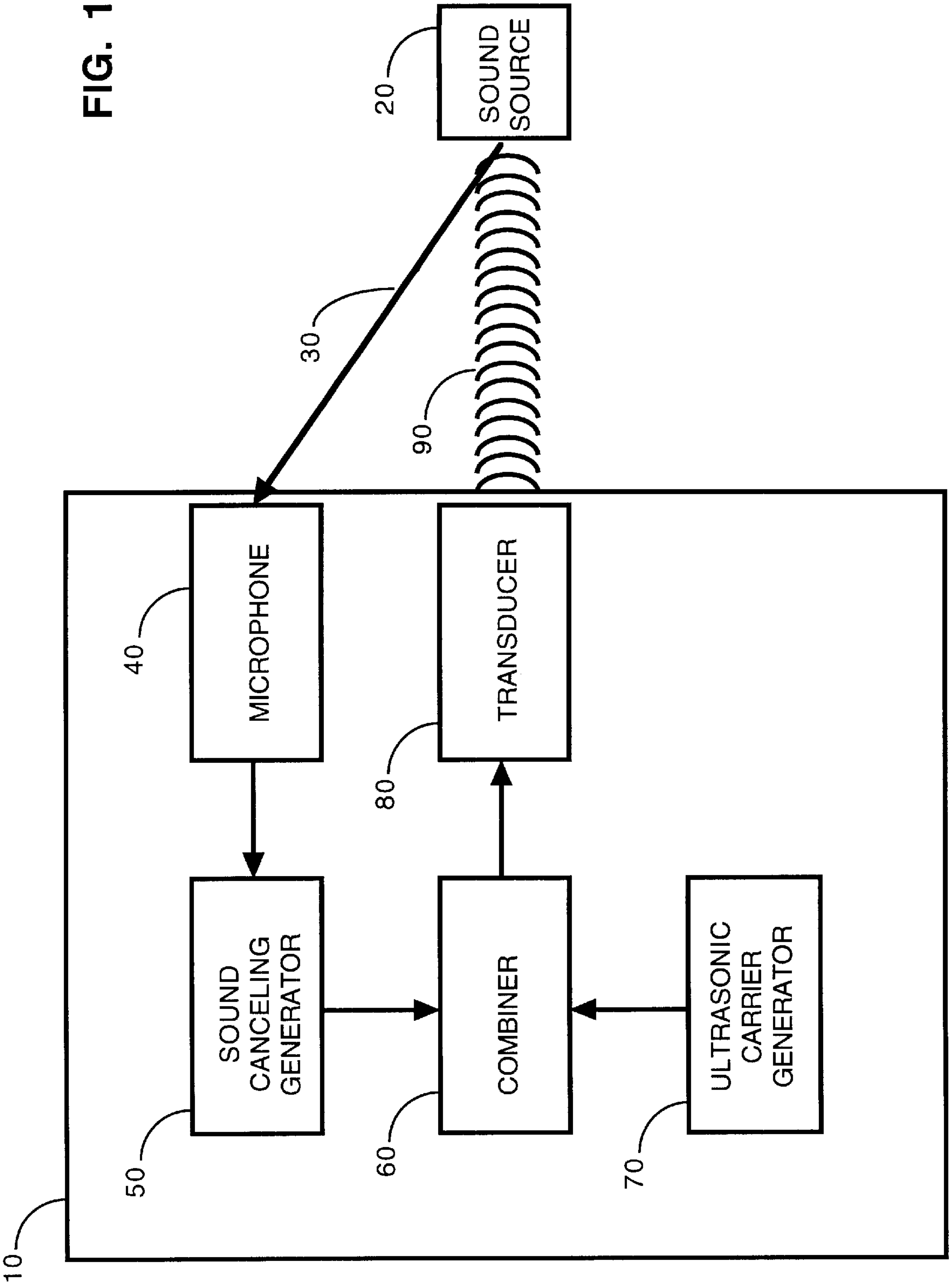
FIG. 1 shows a device for producing an anti-sound beams for canceling sound at the source.

FIG. 1 shows a device 10 for canceling sound at the sound or audio source 20. Sound or sound signal 30 from the sound source 20 is received by microphone 40. The output of the microphone is made available to sound canceling generator 50 which generates a sound canceling signal in response thereto. The sound canceling signal is combined by combiner 60 with an ultrasonic carrier signal from an ultrasonic signal generator 70 to produce a modulated ultrasonic carrier signal, which may be further amplified by combiner 60. Preferably, combiner 60 amplitude modulates the ultrasonic carrier signal with the sound canceling signal. Alternate methods of combining may be used while staying within the scope of the invention. A transducer 80 then converts the modulated ultrasonic carrier signal from the combiner into an acoustical signal 90 having ultrasonic directionality. Acoustical signal 90 having the modulated ultrasonic carrier signal is directed at the sound source, where the sound canceling signal modulated upon the ultrasonic carrier combines with the sound from the sound source to reduce the sound from the sound source.

Microphone 30 is preferably a directional or parabolic microphone for sensing audio generated by sound source 10, and preferably has a directionality substantially equivalent to the anti-sound beam. In this embodiment the canceling sound generator and microphone operate to monitor the sound source and adjust the characteristic of the noise canceling signal in response thereto. Alternately the microphone could be eliminated and the canceling generator could sense a characteristic of of the sound source such a s RPM of a fan motor. Transducer 80 is preferably an ultrasonic transducer. In an alternate embodiment, transducer 80 could have a frequency response which extends into the audio range. In this alternate embodiment, the transducer can generate both the directional ultrasonic modulated sound canceling signal, and audio signals generated by another source such as a radio receiver.

The device of FIG. 1 has the advantage of reducing the sound generated by the sound source at the sound source by adding sound canceling signals with sound substantially at the sound source. The directional characteristics of the anti-sound beam 90 has the advantage of freeing the transducer 80 from being placed in close proximity with the sound source 10. Furthermore, directional characteristics of the anti-sound beam substantially limits the area in which sound canceling sound is present thereby further avoiding additional sound due to the sound canceling device in areas adjacent to the sound source.

Figure 2:
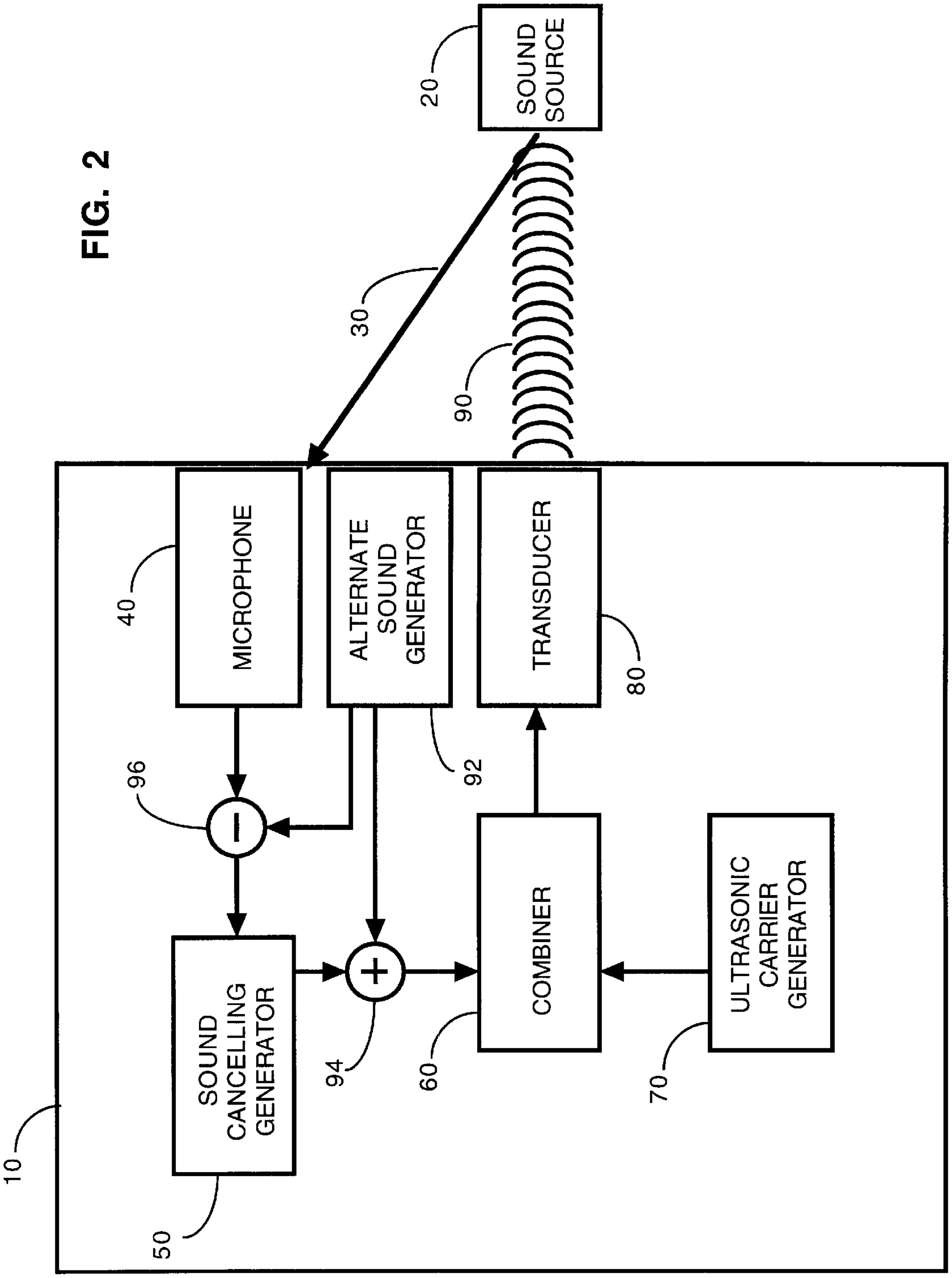
FIG. 2 shows an additional sound generation means added to the device of FIG. 1.

FIG. 2 shows an additional sound generation means added to device 10. Alternate sound generator 92 generates an independent sound and adds the sound to the output of sound canceling generator 50 via summing circuit 94. The output of the summer 94 is then combined with the ultrasonic signal by combiner 60. Transducer 80 then produces a beam 90 that not only has canceling sound but additional sound from sound generator 92. Subtracter 94 then removes sound generated by sound generator 92 from signal received by microphone 40 so that sound canceling generator 50 does not produce canceling sound in response to sound generator 92.

In one embodiment, alternate sound generator 92 can produce a single tone, 1000 Hz for example, in which case subtracter 92 could be a notch filter tuned to 1000 Hz and summer 94 a simple adder. In another embodiment generating of more complex sounds such as music or voice, subtracter 94 would require more complex sound processing. It should be appreciated that summer 94 and subtracter 96 can be incorporated into the sound canceling generator 50 and the combined functionality implemented by a digital signal processor and corresponding software. The device of FIG. 2 has the advantage of not only reducing sound generated by sound source 20, but additional sound from alternate sound generator 92 is produced, effectively substituting alternate sound generated by device 10 for sound from the sound source 20.

Figure 3:
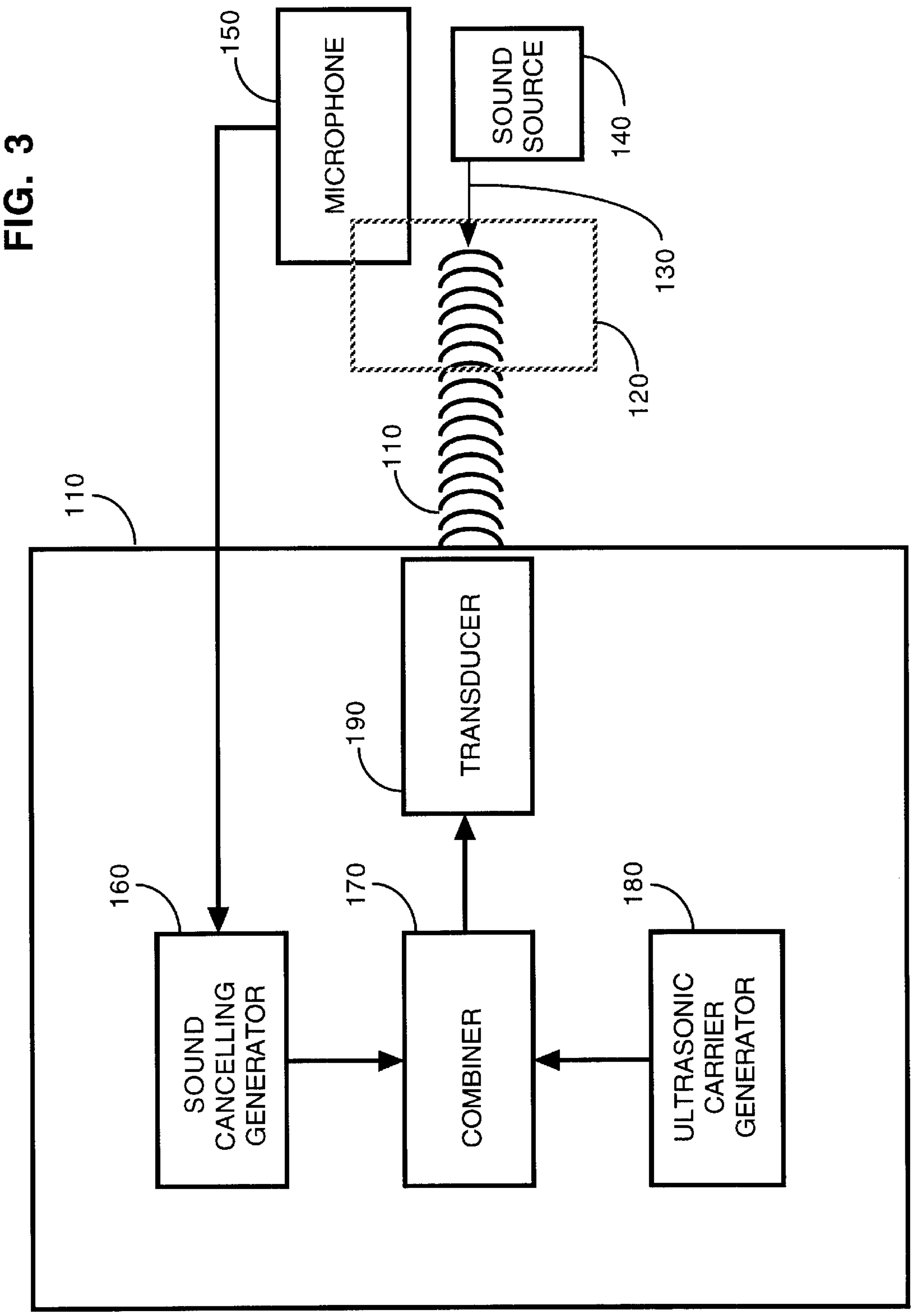
FIG. 3 shows a device for producing an anti-sound beams for canceling sound within a predetermined space.

FIG. 3 shows a device 110 for canceling sound within a predetermined space, shown by dashed area 120. Sound 130 from the sound sources 140 is received by microphone 150 which measures the sound in space 120. The output of the microphone is coupled to device 110 and made available to sound canceling generator 160 which generates a sound canceling signal in response thereto. The sound canceling signal is combined by combiner 170 with an ultrasonic carrier signal from an ultrasonic signal generator 180. Combiner 180 amplitude modulates the ultrasonic carrier signal with the sound canceling signal. Alternate methods of combining may be used while staying within the scope of the invention. A transducer 190 then converts the signal from the combiner into an acoustical signal 200 having ultrasonic directionality, which is directed into area 120 at the sound source, where the sound canceling signal carried upon the ultrasonic carrier combines with the sound from the sound sources to reduce the sound within the area The device of FIG. 3 has the advantage of reducing the sound within area 120 using a remote sound canceling transducer without adding sound to other adjacent areas because of the directionality of the of the canceling sound carried on the beam.

It should be appreciated that alternate sound can be added to area 120 by adding an alternate sound generator and appropriate addition and subtraction functions of 92–96 of FIG. 2 to canceling sound generator 160. This has the additional advantage of not only quieting sound from sound sources 140 within area 120 but also adding an alternate sound to area 120.

I claim:

1. A method of at least partially canceling sound produced by an audio source comprising the steps of:

generating a sound canceling signal in response to the audio source;

modulating an ultrasonic carrier signal with the sound canceling signal to produce a modulated carrier signal;

exciting a transducer with the modulated carrier signal to produce a substantially directional anti-sound beam; and directing the anti-sound beam towards the audio source.

2. The method according to claim 1 wherein said of directing the anti-sound beam towards the audio source at least partially cancels sound produced by the sound audio substantially at the sound source.

3. The method according to claim 1 wherein said step of modulating includes the step of amplitude modulating the ultrasonic carrier signal with the sound canceling signal.

4. The method according to claim 1 wherein the transducer has a frequency response substantially within the ultrasonic frequency range.

5. The method according to claim 1 wherein said step of generating further comprises the steps of:

monitoring the audio source; and adjusting a characteristic of the sound canceling signal in response thereto.

6. The method according to claim 1 further comprising the steps of:

generating an alternate sound signal;

combining the alternate sound signal with the sound canceling signal to generate a combined signal; wherein said step of modulating modulates the ultrasonic carrier signal with the combined signal.

7. The method according to claim 6 further comprising the steps of:

monitoring sound substantially from the audio source to produce a monitored signal;

subtracting from the monitored signal a sound signal indicative of the alternate sound signal to produce a resultant signal, wherein said step of generating the sound canceling signal further comprises the step of:

adjusting a characteristic of the sound canceling signal in response the resultant signal.

8. The method according to claim 6 wherein said step of exciting produces a substantially directional anti-sound beam, and the method further comprises the step of directing the anti-sound beam towards the noise source.

9. A method of reducing sound comprising the steps of:

adding a sound canceling signal modulated upon an ultrasonic carrier with a sound signal to reduce the sound pressure level of the sound signal wherein the sound canceling signal modulated upon the ultrasonic carrier has a substantially directional characteristic and the sound signal is generated by a sound source; and sound, directing the sound canceling signal modulated upon the ultrasonic carrier towards the sound source.

10. The method according to claim 9 wherein said step of directing the sound canceling signal modulated upon the ultrasonic carrier towards the sound source reduces the sound pressure level by canceling sound produced by the sound source substantially at the sound source.

11. The method according to claim 9 wherein the sound canceling signal modulated upon the ultrasonic carrier has a substantially directional characteristic and the sound signal is present within a predetermined space, and the method further comprises the step of directing the sound canceling signal modulated upon the ultrasonic carrier into the predetermined space in order to reduce the sound pressure level of the sound within the predetermined space.

12. The method according to claim 9 further comprising the steps of:

monitoring the resultant of said step of adding; and adjusting ad characteristic of the sound canceling signal in response thereto.

13. The method according to claim 9 further wherein said step of adding further comprises the steps of:

combining with the sound canceling signal with an alternate sound signal to produce a combined signal; and modulating the ultrasonic carrier with the combined signal wherein said step of adding both reduces the sound pressure level of the sound signal while producing a sound pressure level indicative of the alternate audio signal.

14. The method according to claim 13 wherein the combined signal modulated upon the ultrasonic carrier has a substantially directional characteristic and the sound signal is generated by a sound source, and the method further comprises the step of directing the combined signal modulated upon the ultrasonic carrier towards the sound source.

15. A device for reducing sound comprising:

a sound canceling generator for generating a sound canceling signal in response to a sound source;

an ultrasonic carrier generator for generating an ultrasonic carrier signal;

a combiner for producing a combined signal by combining the sound canceling signal with the ultrasonic carrier signal; and a transducer for producing a substantially directional anti-sound beam in response to the combined signal, whereby sound from the sound source is reduced by directing the anti-sound beam towards the sound source.

16. The device according to claims 15 wherein said combiner further comprises an amplitude modulator for amplitude modulating the ultrasonic carrier signal with the sound canceling signal.

17. The device according to claim 15 wherein said transducer is an ultrasonic transducer.

18. The device according to claim 15 further comprising:

a microphone coupled to said sound canceling generator and responsive to sound from the sound source combined with the anti-sound beam for generating a monitored signal, wherein said sound canceling generator produces the sound canceling signal in response to the monitored signal.

19. The device according to claim 15 further comprising:

an alternate sound generator for generating an alternate sound signal; and an adder coupled to said sound canceling generator, said alternate sound generator and said combiner for adding the alternate sound signal with the sound canceling signal, thereby including the alternate sound signal within the combined signal.

20. The device, according to claim 19 further comprising:

a microphone responsive to sound from the sound source combined with the anti-sound beam for generating a monitored signal; and a subtracter for substantially subtracting the alternate sound signal from the monitored signal to produce a difference signal, wherein said sound canceling generator produces the sound canceling signal in response to the difference signal.

* * * * *